(12) United States Patent
Hertha

(10) Patent No.: US 6,652,866 B1
(45) Date of Patent: Nov. 25, 2003

(54) METHOD FOR TREATING DISEASES OF FUNGAL, YEAST, AND PRION PROTEIN ETIOLOGY

(76) Inventor: David W. Hertha, 106 Catina Dr., Meridianville, AL (US) 35759

( * ) Notice: Subject to any disclaimer, the term of this patent is extended or adjusted under 35 U.S.C. 154(b) by 380 days.

(21) Appl. No.: 09/638,115

(22) Filed: Aug. 14, 2000

Related U.S. Application Data

(63) Continuation-in-part of application No. 09/172,949, filed on Oct. 14, 1998, now abandoned.
(60) Provisional application No. 60/062,541, filed on Oct. 14, 1997.

(51) Int. Cl.[7] .............................. A61K 9/00; A61K 9/08; A61K 9/20
(52) U.S. Cl. ........................ 424/401; 424/400; 424/450; 424/464
(58) Field of Search .............................. 424/400, 450, 424/464, 401

(56) References Cited

U.S. PATENT DOCUMENTS

| | | | | | |
|---|---|---|---|---|---|
| 5,120,763 | A | * | 6/1992 | Yehuda | 514/547 |
| 5,194,448 | A | * | 3/1993 | Coupland et al. | 514/558 |
| 5,837,731 | A | * | 11/1998 | Vaddadi | 514/560 |
| 5,945,409 | A | * | 8/1999 | Crandall | 514/78 |

FOREIGN PATENT DOCUMENTS

| | | | |
|---|---|---|---|
| JP | 06287138 | * | 10/1994 |
| JP | 07025760 | * | 1/1995 |

* cited by examiner

Primary Examiner—Thurman K. Page
Assistant Examiner—Rachel M. Bennett
(74) Attorney, Agent, or Firm—Mark Clodfelter

(57) ABSTRACT

A method for treating neurological diseases in mammals comprising the step of administering a mixture comprising selected carboxylic acids in an effective amount for treating the neurological diseases.

19 Claims, No Drawings

METHOD FOR TREATING DISEASES OF FUNGAL, YEAST, AND PRION PROTEIN ETIOLOGY

CROSS REFERENCE TO RELATED APPLICATIONS

This application is a continuation-in-part of U.S. patent application Ser. No. 09/172,949, filed Oct. 14, 1998, now abandoned, which claims the benefit of provisional patent application No. 60/062,541, filed Oct. 14, 1997.

FIELD OF THE INVENTION

This invention relates to treatment and curing of neurological diseases in animals and humans, and particularly to neurological diseases that may be caused by fungus, yeast or prion proteins

BACKGROUND OF THE INVENTION

Diseases of the class relating to spongiform encephalopathies, which include "mad cow" disease and scrapie in animals, and Creutzfeld-Jakob disease (CJD) and possibly some types of Alzheimer's disease in humans, are transmissible conditions affecting nervous systems of mammals, birds and reptiles. Commonly infected species include man, sheep, goats, cows, deer, elk, mink, cats, mice, chickens, and others. In these diseases, and after an incubation period, neurological dysfunctions and death occur due to deterioration of nervous tissue. In some of these diseases, amyloid plaques form in the brain, particularly in Alzheimer's-type diseases, these plaques in some instances being laced with protein fibrils that may resemble a mycelial phase of fungal origin. In other instances, localized areas of neurons in the brain become riddled with lesions and neurons having vacuoles such as those found in certain yeasts. In prion diseases, and from a histochemical standpoint, an infective form of a glycosyl-phosphatidylinositol (GPI)-anchored cell surface prion protein (PrPc) possessing a beta sheet configuration enters neurons of the brain of the host animal and is converted to an aberrant isoform (PrPSc). In this conversion to an infectious form, it has been found that normal GPI proteins, which are found on nerve cells and which possess an alpha helical structure, are converted to the infectious beta sheet configuration by contact with an infectious form of the prion. During replication, the PrPSc beta configuration of the prion is believed to cause vacuolization, swelling and degeneration of neuronal cell bodies and grey matter neuropils, causing lesions and vacuoles in brain tissue of the host animal characteristic of spongiform encephalopathy.

Other neurological diseases in humans such as multiple sclerosis, Parkinson's disease, Huntington's disease, amyotrophic lateral sclerosis, Canavans disease, adreno leukodystrophy, metachromic leukodystrophy, Krabbe disease, Fabry disease, Neimann-Pick disease, Pelizaeus-Merzbacher disease and Guillain-Barre syndrome are believed by Applicant to be caused by yeast, fungi or prion protein-based yeast or fungal structures. In mammals in general, Applicant believes neurological diseases such as Rottweiler leukoencephalomyelopathy, polyradiculoneuritis (coon hound paralysis), degenerative myelopathy in German shepherds, transmissible spongiform encephalopathy and shaker puppies may be caused by yeast, fungi, or prions based upon yeast or fungal structures.

At present, there is no known cure for these diseases. An anti-fungal drug, amphoteracin-b, which is a growth inhibitor, has prolonged the incubation time of scrapie in hamsters, suggesting a fungal, yeast or prion protein-based cause of these diseases. However, this drug is ineffective in ultimately preventing onset of neurological symptoms or halting neuronal destruction and subsequent death of the animal.

Another compound, Congo Red, a stain used in pathological studies to highlight or define amyloid structures in tissues, has been tested as a therapeutic agent. Here, it has been proposed that Congo Red may reduce the number of protein fibrils found in amyloid structures. Additionally, Congo Red may inhibit yeast cell wall production, in turn reducing capacity of the infecting yeast to reproduce. However, Congo Red is not seen as a curative agent for spongiform encephalopathies or other neurological diseases.

Dapsone, an anti-inflammatory drug, may delay clinical signs of CJD but does not delay formation of plaques in Alzheimer-type diseases. Also, Dapsone may hinder macrophage processing of the CJD agent. As one possible infection route, biting insects such as sheep keds, hay mites, ticks and others have been implicated as naturally occurring vectors for transmission of fungal, yeast or prion diseases. Practices of feeding domestic animals fodder containing animal protein (offal containing neurological tissue) have been studied as well, and are correlated with transmission of certain prion diseases such as mad cow disease and scrapie. Here, although offal is cooked or rendered, killing bacteria and most viruses, prions are known to withstand temperatures of up to 600 degrees Fahrenheit or so.

Lyme disease, a tick-borne disease caused by the bacteria *Borrelia burgdorferi*, is conventionally treated with antibiotics. However, a large percentage of patients diagnosed with Lyme disease have later shown forms of dementia similar if not the same as the dementia demonstrated by victims of Alzheimer's disease. While the bacteria *Borrelia burgdorferi* is the causative agent of Lyme disease, the cause of subsequent dementia after resolution of the Lyme disease has not been determined. Here, Applicant proposes that a single tick with an attachment time of about 18 hours or so, the time it takes for an attached tick to become engorged, could serve as a vector for fungal, yeast or prion diseases that are manifested months to years after initial infection by the tick vector.

In one study of tick haemolymph analysis, valine, inositol and glucose were appreciably higher in concentration than other amino acids and sugars, valine, inositol and glucose also being found in yeasts and fungi, suggesting that ticks and other biting insects may harbor infectious yeasts and/or fungi. Additionally, valine, inositol and glucose are found in prion proteins, also suggesting a link between yeast, fungi and prions. Further, in mammals in general including humans, fungi and yeast are common skin-dwelling organisms. Ticks often migrate to the head and neck region, which is also an area proximate an abundance of neurological tissue rich in sugars such as glucose, a preferred food source of yeasts. As such, yeast or fungal cells may be introduced at the head or neck region of an animal by ticks or other biting insects.

One possible causative yeast suggested by Applicant, *Saccharomyces cerevesiae* (SC), generally regarded to be normal flora to both human and animals, and commonly used in brewing and baking, bears significant similarities to prions. Both prions and SC are resistant to formaldehyde, are resistant to temperature extremes, have glycosyl-phosphatidylinositol (GPI) protein surface anchors, and have glucose and mannose as surface sugar components. Glucose and mannose as surface sugars may aid in sc ingestion by host macrophages. Here, it may happen that a macrophage does not kill the ingested yeast, but inadvertently transports the yeast to a part of the body where the yeast gains access to the central nervous system of the host. It may also happen that some process within the macrophage initially converts the yeast into a prion protein.

Significantly, GPI protein surface anchors are also found on the surface of mammalian nerve cells. SC can also synthesize methionine and valine, it being noted that in the infective form of many prions that have been studied, methionine or valine is substituted for another amino acid at codon 129 of the prion protein. Further, SC has receptor sites for hormones such as insulin, human chorionogonadotropin and estradiol. Another feature of SC is the production of trehalose, a disaccharide composed of two glucose molecules. In general, trehalose provides thermoprotection to the yeast cells, and further provides thermoprotection to proteins of non-yeast origin, such as bovine serum albumin. Trehalose is also used to protect mouse embryos from dehydration and during freezing, and is found in tick haemolymph, another suggestion that ticks may harbor yeast and/or fungi that may infect mammals. Further, ceramide, a protein manufactured by cells in the central nervous system of mammals, may be used by SC to manufacture trehalose. Since SC manufactures trehalose, it may be that trehalose is manufactured by prion proteins of SC or other yeast or fungal origin, thus providing the observed thermal resistance of prions.

DETAILED DESCRIPTION OF THE INVENTION

As stated above, Applicant proposes that a prion infection may be caused by the yeast SC, or other yeasts or fungi, on occasion being conveyed through the skin and into the blood and body of a mammal by a biting insect. Once in the body of a host, the yeast or fungi may enter a mycelial form that is very difficult to detect. In this form, the DNA of SC is very diffused, and often escapes detection even by electron microscopy. In the host, the yeast DNA may occasionally be incorporated into a nerve cell, which being an environment rich in glucose, promotes replication. Yeast may also be involved in infective prion formation. Here, in the process of manufacturing GPI, which as stated is a surface protein normally found on SC and other yeasts, the yeast DNA may substitute a valine or methionine amino acid at codon 129, possibly because the proper amino acid is not present in the host nerve cell or other factors related to the environment of a nerve cell. The result of this substitution may contribute to forming a prion protein configured not in the normal non-infective alpha helical configuration but the infective beta sheet configuration. As more of the GPI-based prion proteins accumulate, vacuoles form in infected nerve cells, causing them to swell and eventually burst, releasing the infective prion proteins to become incorporated into surrounding nerve cells. Such destruction of nerve cells may be due to abnormal uptake of calcium. Here, it has been discovered by other researchers that codons 105–126 of infectious prion proteins are involved with a chemical mechanism wherein permeability of nerve cells to calcium is lowered, causing an excessively high inflow of calcium into the cell, resulting in the cell swelling and eventually bursting. As such, administration of potassium to an affected mammal to maintain blood potassium levels at or near an upper limit for that species may reduce or assist in regulating permeability of nerve cells to calcium. Amounts of potassium administered to a mammal to raise blood levels to a point at or near an upper limit for that species is determined by blood chemistry analysis and monitoring, as should be apparent to anyone skilled in the medical arts. Such administration of potassium to a mammal is contemplated to be used in conjunction with treatment with carboxylic acids as described herein.

Other diseases that Applicant believes may be caused directly (or indirectly as by stimulation of an immune response) by prions or yeast include demylinating diseases such as multiple sclerosis in humans, and in dogs, Rottweiler leukoencephalomyelopathy and polyrediculoneuritis. In these diseases, the myelin within the myelin sheath around nerve fibrils is dissolved or otherwise eroded away, causing the nerve fibril to cease functioning. These diseases are given as examples of the class of demyelinating diseases for which Applicant has treated, as will be further explained, it being noted that other demyelinating diseases are probably treatable by Applicant's method.

For treating the described neurological diseases believed by Applicant to be caused by yeast, fungi and prion proteins, Applicant proposes treatment using one or more fatty acids from the group of carboxylic acids C-2 through about C-22, which includes decanoic, nonanoic, octanoic, heptanoic, hexanoic, pentanoic, butyric, propionic and acetic acids. Additionally, one or more of the analogs of these fatty acids may be included in a therapeutic mixture or used by itself to treat a particular neurological disease. In one delivery method of the invention, one or more of these acids, with possibly one or more of their analogs, may be applied to the skin about the head, neck and back of the subject. This area of skin is proximate the skull and spine of the subject, i.e. the infected neurological areas. In this delivery method, decanoic and octanoic acids increase permeability of the skin, allowing other compounds including the described fatty acids to penetrate the skin and enter the bloodstream. Additionally, other vehicles such as DMSO or pleurolecithin organogel (PLO) may be used to increase permeability of the skin. This increased permeability caused by these compounds may be an interaction of the lipophilic liquids with the lipid bilayers of the stratum corneum, leading to decrease of barrier resistance of the skin. Advantageously, decanoic and octanoic acids, in addition to hexanoic and nonanoic acids, are insecticidal to many insects including acarina (ticks and mites). Further, octanoic acid is anti-yeast, and can cross the blood-brain barrier, after which it enters astrocytes and is metabolized. Decanoic acid is a bi-functional protein cross-linking agent, which is believed to convert a beta sheet configuration of infective prions to non-infective alpha helical configurations. Further, decanoic acid is anti-fungal and has anti-tumoral properties, and is toxic to trypanosomes. Here, the toxic action of decanoic acid is on the GPI surface anchors of the trypanosomes, these surface anchors being similar to the GPI surface anchors of SC and prion proteins. As such, decanoic acid should be effective against any neurological disease caused by yeast or infective prion proteins having GPI surface anchors. In addition, others of the discussed carboxylic acids bind to proteins, with butyric acid showing greatest stability as a cross-linking agent to form alpha helical structures. Thus, butyric acid may be one ingredient in a therapeutic compound. Acetic acid is anti-yeast, and heptanoic acid, when given orally, is a glucose-lowering agent. By lowering glucose levels, yeast metabolism is inhibited. Analogs such as 12-methyl tetradecanoic acid possess anti-fungal properties, and 17-methyl octadecanoic acid is used in remyelinization of nerve fibers. 20-methyl heneicosanoic acid and docosanoic acid may have a high velocity in alpha hydroxylation processes that synthesize cerebrocides, a class of compounds that are building blocks for myelin. As such, these compounds should be useful treating subjects recovering from demyelinating diseases. In addition, other compounds may be included in a therapeutic mixture, such as myristic acid, which is toxic to trypanosomes and may repel mites and other biting insects. Palmatic acid, 14-methyl hexadecanoic acid and octadecanoic acid are beneficial to the skin, and help prevent irritation thereto during treatment.

The following is a list of carboxylic acids that are believed useful in treatment of neurological diseases which may be caused by yeast, fungi or prions based on yeast or fungal etiology:

acetic acid
propanoic acid
2-methyl propanoic acid
butanoic acid
2-methyl butanoic acid
4-methyl pentanoic acid
hexanoic acid
heptanoic acid
octanoic acid
4-ethyl octanoic acid
nonanoic acid
decanoic acid
dodecanoic acid
tridecanoic acid
tetradecanoic acid
12-methyl tetradecanoic acid
pentadecanoic acid
14-methyl pentadecanoic acid
hexadecanoic acid
14-methyl hexadecanoic acid
octadecanoic acid
9-octadecanoic acid
17-methyl octadecanoic acid
9, 12-octadecadienoic acid 18-methyl nonadecanoic acid
eicosanoic acid
18-methyl eicosanoic acid
20-methyl heneicosanoic acid
docosanoic acid
13-docodanoic acid The listed mixture of compounds may be used in various combinations and in any proportion for the treatment of yeast/fungal/prion infections. Such combinations may be applied topically to the subject, particularly to the head and neck areas avoiding eyes and mucus membranes. Also, it may not be necessary to include all of the ingredients in a mixture used to treat the described neurological diseases. In fact, it may be that only one of these compounds is needed to treat a specific neurological disorder or disease.

In order to enhance effects of the described fatty acids against prion proteins, yeast and fungi, other therapeutic measures that may be taken include lowering the oxygen level and glucose level of the subject. Here, lowering of the oxygen level of the blood of the subject may increase toxicity to yeast by inducing production of hydrogen peroxide within the yeast, while lowering blood glucose levels increases rate of hydrogen peroxide production in the yeast and decreases available food source for yeasts. For decreasing oxygen blood levels, and where practical, herds may be taken to higher altitude lands where rarified air decreases oxygen levels in the blood of animals. Alternately, animals may be placed in an environment enriched in carbon dioxide or nitrogen to simulate the rarified air of a high altitude environment. Further, blood oxygen may be reduced somewhat by causing the animals to cry out, as by mimicking calls of that species. Lowering of glucose levels may be accomplished by fasting and withholding of water. Here, fasting would lower glucose levels in the blood, forcing the body to utilize alternate sources of energy. In this instance, increased metabolism of the fatty acids used as a treatment would result, increasing exposure of the cells to these fatty acids. Particularly, nerve cells are known to metabolize octanoic acid. Duration of fasting would depend on the animal, and may be in the range of 4–10 days or so. Here, a cow with relatively abundant body fat may have food withheld for up to 10 days, while an animal with faster metabolism may have food withheld for 3–4 days or so. A human may fast for a week to 10 days or so without harm, thus such a length of time may be incorporated into a treatment for humans. Withholding of water may concentrate the available carboxylic acids in the blood, and may be done for 1–2 days at a time. Fasting and withholding of water may be repeated during treatment, say once a month. Dieting restrictions may occur between periods of fasting.

As stated, treatment of two dogs having neurological diseases has been performed. Here, by way of example, a mixture of the following carboxylic acids was prepared.

| | |
|---|---|
| acetic acid | 11 cc |
| propionic acid | 4 cc |
| methyl acrylate | 15 cc |
| butyric acid | 13 cc |
| hexanoic acid | 2 cc |
| heptanoic acid | 3 cc |
| octanoic acid | 6 cc |
| ethyl octanoic acid | 9 cc |
| nonanoic acid | 2 cc |
| decanoic acid | 6 cc |
| heneicosanoic acid | 400 mg |
| docosanoic acid | 400 mg |
| lecithin isopropyl palmitate | 90 ml |

Approximately 20% pleurolecithan organogel was added to form a total weight of the mixture of 454 grams.

In this mixture, decanoic, hexanoic, octanoic and ethyl octanoic acids were selected for their anti-fungal and anti-yeast properties, these acids also being able to cross the blood/brain barrier and enter nerve cells. C2–C10 are selected for their protein cross-linking properties, and heneicosanoic and docosanoic acids were selected for their properties that assist in rebuildingmyelin. Of these compounds, decanoic acid is a solid that when melted and mixed with the others remains dissolved in a liquid form. Heneicosanic acid and docosanoic acid are in powder form. Lecithin isopropyl palmitate serves as a vehicle to assist in transporting the mixture through the skin, and the pleurolecithin organogel causes the mixture to form a gel or jelly-like consistency. These compounds were mixed to a smooth and uniform consistency in a mixing device similar to a blender, as should be apparent to anyone skilled in the pharmaceutical arts.

The first dog, a Rottweiler of about 120 lbs., had contracted Rottweiler leukoencephalomyelopathy, a demyelinating neurological disease specific to Rottweilers and considered to have a fatality rate of 100%. This disease is characterized by general deterioration of the animal over a period of about 7 months or so, after which the dog usually either dies from an infection or is euthanized. At the time treatment was initiated, the dog could barely stand on a rough surface, and could not walk across a smooth floor surface without falling. A mixture of carboxylic acids believed most important for a treatment was prepared as described above, and treatment of the dog, which as stated was about 120 lbs., entailed rubbing approximately 2–6 tablespoons of the mixture into the skin over the head, neck and spine of the dog once daily. Here, the object was to coat the skin, and possibly massage it in, over the head, neck and spine so as to allow penetration of the mixture through the skin and into the system as proximate as possible to the central nervous system.

The dog responded favorably to the treatment, and after the first day was noticeably stronger, and could walk on a tile floor. His strength returned over a period of about 3 weeks, at which point the dog was walking without undue effort and could run a short distance. Over a period of about 2 years, treatment was discontinued 5 times for periods ranging from 1–2 weeks, which resulted in dramatic regression. Each time treatment was resumed, the dog's condition improved. Treatment was also varied from a once daily topical application to once every other day to about 2–3 times a week. In the course of treatment, it was discovered that the dog's condition would improve when treated daily, and the dog's condition could be maintained if treated every other day or so. As this dog was relatively old, the owners decided at about 2.5 years after onset of the disease to euthanize the dog. At this point, treatment had been discontinued and the dog could barely walk on a tile floor.

Alternately, ½ to 1 lb. of the mixture may be used to cover the skin of the entire animal. This may be useful in treating livestock such as sheep. Of course, the actual quantity of mixture is not as important as using a sufficient quantity to cover at least the head, neck and spine, and possibly a larger area of the skin surface of the animal.

In alternate administrations of Applicant's treatment, and for a mammal of about 120 lbs., Applicant proposes to administer from about 1–5 grams of the mixture orally on a daily basis, preferably mixed with feed or in a capsule or pill form. The dose may be divided into portions and given with a meal in the morning and at night. To prevent attack by digestion in the stomach, the mixture may be prepared in a time-release form so as to pass through the stomach substantially unchanged and be released in the intestinal tract so as to be absorbed thereby, as should be apparent to one skilled in the art. Ingestion of the mixture may also be accompanied by topical application as described. Further, injectable forms of the mixture may be prepared, such as 50–100 mg mixed in a liter of diluent. Such an amount of this solution may be administered by IV drip on a daily basis, and may be used in conjunction with topical application and/or oral administration.

The other dog, a 50 lb. Dalmation, was afflicted by polyradiculoneuritis (coon hound paralysis), another demeylinating neurological disease. In this disease, the dog usually experiences paralysis of its limbs for 6–12 weeks or so while retaining sensory perception therein. In addition, the disease may be fatal due to respiratory paralysis. A mixture of carboxylic acids was prepared as described above, and about 2 oz. was applied topically once a day on the skin over the head, neck and spine of the animal. At the time treatment was initiated, the dog had no motor functions in its legs, although it had sensory perception in its legs. The dog also had ascending paralysis resulting in respiratory difficulty, and could barely hold up his head. Almost immediately after treatment was begun, within 8 hours or so, the dog's respiration had improved, and could easily hold up its head. After 4 days the dog could crawl on its "elbows". After 20 days the dog could bear its own weight on its legs, and after 23 days the dog could walk.

In a human subject with a 25 year history of multiple sclerosis, yet another demeylinating disease, a mixture of carboxylic acids prepared as described above was topically applied to the upper back and lower neck of the subject. The quantity applied daily was from about 2–3 tablespoons, with treatment lasting about 45 days. At the time treatment began, the subject had a tremor in one arm, could not button his shirts and could only walk with difficulty with the assistance of a walker and then only a short distance. He could not lift his feet 5 inches or so to the floor of a motorized wheelchair. Within about 24 hours after treatment was begun, the man could button his shirt and the tremor had decreased markedly. His walking had improved, although he still needed to use the walker. The number of times he used the walker and distance he walked also increased, and he was able to lift his feet to the floor of the motorized wheelchair. In addition, family members stated that during treatment his condition and mobility was the best it had been in years. Treatment was terminated after about 45 days, after which the man relapsed to his prior condition of almost being bedridden, and a full-time caregiver was hired.

In all of the subjects, no adverse symptoms were noted, which should be expected since some of these carboxylic acids are used in the cosmetic industry, such carboxylic acids having already been exhaustively tested for adverse or harmful effects. In addition, while specific amounts and ingredients are given, it should be apparent that proportions of these ingredients may be changed. Further, some of the ingredients of the described mixture may be omitted, or other carboxylic acids substituted therefor.

Treatment of other neurological diseases, particularly Alzheimer's disease in man and transmissable spongiform encephalopathies in man (CJD) and mammals (mad cow disease, scrapie, etc) may be implemented as described above. In these instances, and for humans, the described mixture of carboxylic acids may be topically applied to the neck and back once daily using an amount (3–6 tablespoons) sufficient to coat the skin over these areas. Such treatment would be continued as long as necessary to either maintain a neurological condition of the affected individual or effect a cure. In addition, the topical application may be accompanied by IV and/or oral administration of the mixture. In this instance, the oral dosage of 1–5 grams daily should suffice, as would 1 liter of approximately 5% solution of the compound administered by IV drip daily. For livestock, treatment for mad cow, scrapie, etc. would also be as described, with quantities of the mixture used depending on size of the animal. In addition, periods of fasting and withholding of water may be done as described.

Yet another use of the described carboxylic acids is in the treatment of mites in honeybees. Here, the mixture may be adjusted to contain carboxylic acids having mite-repelling properties and properties beneficial to the nervous system of bees. Such a mixture would be incorporated in a greasecake, which then would be introduced to a hive of bees as would be apparent to a beekeeper.

Having thus described my invention and the manner of its use, it should be apparent that changes may be made thereto that fairly fall within the scope of the following appended claims, wherein I claim:

1. A method for treating diseases in mammals such as Crutzfeld-Jakobs disease in humans, scrapie in sheep and goats and bovine spongiform encephalopathy in cattle comprising the steps of admninistering a mixture comprising carboxylic acids from C2–C22 in an amount effective for treating said Crutzfeld-Jakobs disease, said scrapie and said bovine spongiform encephalopathy.

2. A method for treating diseases in mammals such as Rottweiler leukoencephalomyelopathy in Rottweilers, muscular dystrophy in humans, Creutzfeld-Jakob disease in humans, scrapie in sheep and goats and bovine spongiform encephalopathy in cattle comprising the step of administering a mixture comprising carboxylic acids from about C2–C4, C6–C10 and C21–C22 in an amount effective for treatment of said diseases.

3. A method as set forth in claim 1 further comprising the step of including methyl acrylate and ethyl octanoic acid in said mixture.

4. A method as set forth in claim 3 further comprising the step of daily applying about 2–6 tablespoons of said mixture to skin of a head, neck and back of said mammals.

5. A method as set forth in claim 3 further comprising the step of applying between about ½ to 1 pound of said mixture to cover skin of said mammals.

6. A method as set forth in claim 3 further comprising the step of preparing said mixture for oral administration and orally administering about 1–5 grams of said mixture daily to said mammals.

7. A method as set forth in claim 3 further comprising the step of withholding food for a selected period of time from said mammals.

8. A method as set forth in claim 3 further comprising the step of lowering oxygen levels for a selected period of time in said mammals.

9. A method for treating spongiform encephalopathy in mammals, such as Crutzfeld-Jakobs in humans, scrapie in sheep and goats and bovine spongiform encephalopathy in cattle comprising the steps of:

forming a mixture of compounds including carboxylic acids from about C2–C4, C6–C10, C21 and C22, said compound comprising a substance for transporting said carboxylic acids through skin of said mammals, applying said mixture to skin areas of said mammals.

10. A method as set forth in claim 9 further comprising the step of adding methyl acrylate and ethyl octanoic acid to said mixture.

11. A method as set forth in claim 10 further comprising the step of applying said mixture in an amount sufficient to cover skin surfaces of a head, neck and back of said mammals.

12. A method as set forth in claim 10 further comprising the step of preparing said mixture as an injectable solution, and injecting into said mammal a sufficient quantity of said mixture to treat said mammals.

13. A method as set forth in claim 10 further comprising the step of preparing said mixture so that it may be orally administered, and orally administering a sufficient quantity of said mixture to treat said mammals.

14. A method as set forth in claim 10 further comprising the step of withholding food for selected periods of time from said mammals treated with said mixture.

15. A method as set forth in claim 14 further comprising the step of lowering an oxygen level of said mammals.

16. A method as set forth in claim 2 further comprising methyl acrylate and ethyl octanoic acid in said mixture.

17. A method as set forth in claim 16 further comprising the step of including in said mixture an agent for promoting absorption of said mixture through a skin surface of said mammals, and applying said mixture to said skin surface.

18. A method as set forth in claim 16 further comprising the step of preparing said mixture for oral administration and orally administering said mixture.

19. A method as set forth in claim 16 further comprising the step of preparing said mixture for injection and injecting said mixture.

* * * * *